US009398937B2

(12) United States Patent
Guez et al.

(10) Patent No.: US 9,398,937 B2
(45) Date of Patent: *Jul. 26, 2016

(54) OPERATING ROOM ENVIRONMENT

(71) Applicant: ControlRad Systems, Inc., Radnor, PA (US)

(72) Inventors: Allon Guez, Penn Valley, PA (US); Haim Melman, Kefar Sava (IL); Nir Eden, Haifa (IL); Nitai Dean, Astoria, NY (US)

(73) Assignee: ControlRad Systems, Inc., Radnor, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,830

(22) Filed: Aug. 10, 2015

(65) Prior Publication Data
US 2015/0346819 A1 Dec. 3, 2015

Related U.S. Application Data

(63) Continuation of application No. 14/222,982, filed on Mar. 24, 2014, now Pat. No. 9,131,989.

(60) Provisional application No. 61/804,631, filed on Mar. 23, 2013.

(51) Int. Cl.
*G09G 5/00* (2006.01)
*A61B 19/00* (2006.01)
*G06K 9/00* (2006.01)
*G06F 3/01* (2006.01)

(52) U.S. Cl.
CPC ............ *A61B 19/5244* (2013.01); *A61B 19/56* (2013.01); *G06F 3/013* (2013.01); *G06K 9/00604* (2013.01); *G06K 9/00671* (2013.01); *A61B 2019/5255* (2013.01); *A61B 2019/5272* (2013.01); *A61B 2019/568* (2013.01); *A61B 2034/2055* (2016.02); *A61B 2034/258* (2016.02)

(58) Field of Classification Search
CPC ......... G06F 3/011; G06F 3/012; G06F 3/013; G06F 3/0416; G06F 3/038; A61B 19/5244; A61B 2019/5255; A61B 2019/5272; A61B 19/56
USPC .......................................... 345/156–158, 204
See application file for complete search history.

(56) References Cited

U.S. PATENT DOCUMENTS

| 7,702,379 B2 * | 4/2010 | Avinash | A61B 5/06 378/116 |
| 7,835,498 B2 * | 11/2010 | Bonfiglio | A61B 6/00 378/115 |
| 9,131,989 B2 * | 9/2015 | Guez | A61B 19/5244 |

(Continued)

FOREIGN PATENT DOCUMENTS

| EP | 0631222 A1 | 12/1994 |
| WO | 2009056921 A2 | 5/2009 |

OTHER PUBLICATIONS

International Search Report and Written Opinion in PCT/US2014/031636 dated Aug. 18, 2014.

*Primary Examiner* — Jennifer Nguyen
(74) *Attorney, Agent, or Firm* — Manelli Selter PLLC; Edward J. Stemberger

(57) ABSTRACT

A method serves to facilitate communication between members of an operating team in an operating room. Among others the method supports operation of different devices and expression of different command by gazing at a proper area on the monitor.

20 Claims, 5 Drawing Sheets

(56) References Cited

U.S. PATENT DOCUMENTS

2010/0167248 A1* 7/2010 Ryan .................. H04N 7/181 434/262

2012/0146891 A1* 6/2012 Kalinli .................. H04N 19/33 345/156

* cited by examiner

OPERATING ROOM ENVIRONMENT

This application is a continuation application of U.S. application No. Ser. No. 14/222,982, filed on Mar. 24, 2014, which claims the benefit of priority to U.S. application Ser. No. 61/804,631, filed on Mar. 23, 2013, all of which are incorporated herein by reference in their entireties.

TECHNOLOGY FIELD

The system relates to method and apparatus for supporting and coordinating teams of different medical specialists in an operation room environment and in particular in a catheterization laboratory (cath lab) procedure room.

BACKGROUND

Eye tracking systems have been developed to interact with electronic devices such as personal computers, automobile control systems, and other automation systems. In general, such systems allow team members to issue commands to electronic devices by gazing at a determined area of a monitor or display. Use of eye tracking systems capable of activating and operating electronic devices reduces the amount of verbal communication or gestures that are required to convey a desired message or a desired command to the selected electronic device.

Initially, such eye tracking systems have found use as interfaces to devices to be operated or used by handicapped or otherwise impaired persons, although the technology has gradually spread to other applications, where it still offers some limited command capabilities.

Recently, in addition to eye tracking systems, interfaces capable of recognizing hand gestures hove became available, for example, Microsoft Kinect system and others. Methods and system combining different types of non-contact man-machine interfaces are fast developing and are disclosed for example in the EyeMax+ from DynaVox Mayer-Johnson, combining speech and eye inputs to allow disabled persons to control a computer.

Such non-contact man-machine interfaces could be desirable in the modem operating room environment, where relatively large teams of different medical profession specialists perform a surgical or diagnostic procedure using a relatively large number of instruments or machines. These interfaces could reduce the amount of verbal and prone to misinterpretation communication, their protocol could be set according to certain predefined protocol setting either according to team hierarchy or procedure sequence. Such interfaces could replace the existing system operating buttons, keyboards or touch type monitors used by some operating team members to perform different procedures and protocols. Reduction in contact type operated processes and verbal communication could preserve sterility in the operating room.

SUMMARY

A system for monitoring and controlling a medical procedure and in particular activities of a multidisciplinary operating team working in an operating room. The system could include one or more monitors configured to display different images including the image of a treatment area, the tissue to be manipulated and a treatment tool. The system also includes a plurality of operating team members tracking devices. Each tracking device could be characterized by a field of view of the viewing box. Each tracking device is configured to track at least one uniquely identified team member. An example of a team member tracking device is an eye tracker, providing the gaze location of at least one uniquely identified team member relative to the one or more monitors. The activities and movements of the operating team members could cause a situation where some tracking devices viewing boxes would have partially overlapping area. Each operating team member identifier is associated with each team member. Such identifier could be anatomical characteristics of the team member, pressure developed by at least one limb of the team member, and an artificially generated identifier. The team member identifier could include data on team member hierarchy, team member functionality, team member authorizations and other team member activities.

When the operating team member changes or moves from one physical location to another location, the originally associated with the particular team member tracking device passes on or transfers the team member identifier and team member monitoring to another team member tracking device. Typically, such transfer of monitoring could take place when the overlapping field of view of the respective viewing boxes would be about 75%. Alternatively, the transfer of monitoring could take place when the probability of the team member identification by the second team member tracking device is higher than a preset value. Different criteria could be applied to the probability of the team member identification. In one example, the probability of team member identification could be based on an arithmetical average of at least 20 last team member identifications.

The transfer of monitoring by one team member tracking device to a another team member monitoring device could include data on team member hierarchy, team member functionality, team member authorizations and other team member related issues. The team member tracking devices are configured to distinguish between different team members and provide location coordinates of a uniquely identified team member to another tracking device. For example, X2 Eye Trackers from Tobii Technology AB S-182 17 Danderyd Sweden or similar provides the location of the team member relative to the viewing box. Some team member tracking devices could be configured to serve as a master tracking device. Such master tracking device could be configured to track simultaneously a plurality of the team members. For example, a Kinect could serve as such a master tracking device, and provide location coordinates for a plurality of team members to the other team member tracking devices.

The system facilitates communications between the operating team members. One or more monitors could be configured to display in addition to the image of the treatment area auxiliary images of soft touch buttons. The monitor or at least the images of soft touch buttons could be configured to be responsive to team member gaze. The response to a team member gaze could include activation of a system processes, centering the displayed image about the treatment tool, change of the treatment selection or configuration, and instructions to other team members. The response to a team member gaze could activate the treatment recipient support and convey to the support commands to translate horizontally, translate vertically and tilt to hone in on coordinates provided by the tracking device.

DETAILED DESCRIPTION

Figure 1:
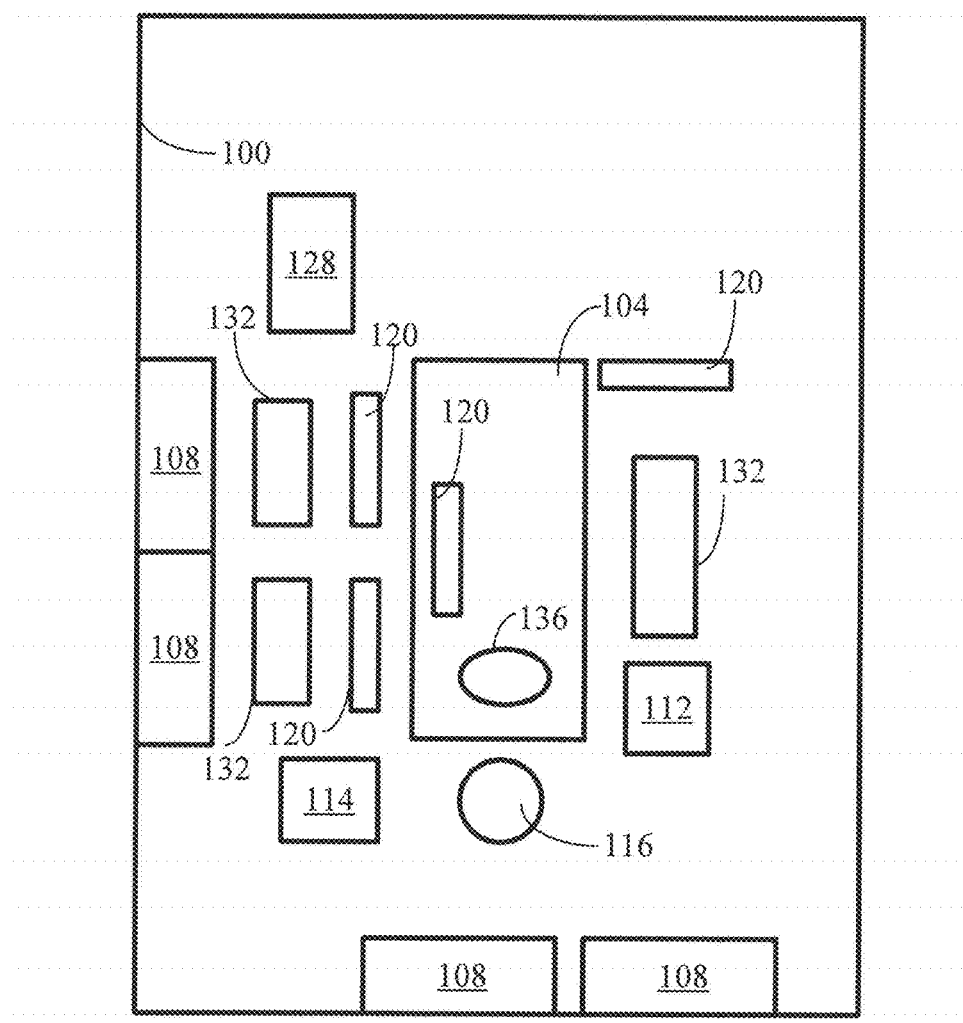
FIG. 1 is a schematic representation of an operating room environment according to an example.

As illustrated in FIG. 1, a catheterization laboratory (cath lab) procedure room 100 usually includes a raised table or support 104 where the treatment recipient is placed. The support 104 is typically placed in the center of the room and can be moved horizontally, vertically, and tilted in any direction. Different raised table or support 104 accessories such as arm boards and extenders, and a large number of in-room storage cabinetry 108 that stores catheters, guiders, balloons, stents and guidewires, a counter space, a clinical sink, computer drops for connection to one or more of local computers 112 and a central computer. Some of the computers could be networked or be standalone computers, some of which could serve as controllers for different equipment present in the room. The cath lab also includes anesthesia equipment, digital imaging equipment such as X-ray 116 or other imaging modalities equipment for fluoroscopy and cineangiogram that allow for precise assessment of the treatment recipient cardiac and cardiovascular problems. One or more networked or standalone monitors 120 some of which could display on their screen images of the treated area and some of which could be used to operate the equipment in the operation room and serve as controllers for different equipment present in the room. Specialized cardiac operation rooms could include diagnostic imaging systems such as MRI system 128 to assist surgeons in specialized cardiac procedures. A number of tables 132 on which different sterilized and used instruments or operation materials could be placed are dispersed around table 104. A computer controlled lights 136 are used to provide bright light, without shadows, during surgery. A breathing machine could be present in the operation room and a computer controlled gas mixer to control the mixture of gases in the breathing circuit.

A typical cath lab surgical or operational team includes physicians of different professions, nurses and certain engineering personnel. In course of a surgical procedure the surgical team or at least some of the team members can typically observe or view the procedure on one or more of the monitors 120. In course of a surgical procedure, the operating team, or at least one of the team members could be required to make a number of decisions, which affect the outcome of the surgical procedure. The decisions could include selection of region of interest (ROI), operating tool selection, record notes or issue commands to other operating team members.

Because multiple devices are controlled by verbal commands to the operating team members, the surgeon or other operating team member must verbally convey both an indication of which device he or she desires to control and an indication of what action he or she wishes the device to perform. This tends to be complicate, time-consuming, error prone, and often requires the team member to remember a large vocabulary of very specific words, phrases, or names, to clearly distinguish between the multiple devices being controlled by the team member.

As described in more detail herein, the present system supports use a non-verbal and a non-contact system operation. It can simplify the communication process between different operating team members, provide easy and convenient operation of different apparatuses and devices present in the operating room, and result in reduced errors and misunderstandings between operating team members and improve the quality of the operation process to ensure its positive outcome. Among others, the system utilizes eye tracking technology for recognition of authorized operating team members instructions as well as to receive similar (eye tracking) input from other team members. By receiving input from different team members in this manner, the system could support the team members to communicate with the systems and between the team members more naturally, thereby reducing the amount of errors, keeping a more sterile environment and reducing fatigue of the team members during the course of long surgical operations.

In some examples the team members could switch between them their roles and tasks. For example, one of the team members begins introduction of a catheter, while another team member introduces a balloon into the cardiac space. Operating team members supervising activation and use of different auxiliary equipment such as X-ray 116, MRI system 128 or computer controlled lights 136 could also exchange roles and activities between them.

The processing unit is configured to produce the control signal based on the position estimate of the at least one team member eye, such that the illumination area includes the position estimate, either of at least one eye actually registered by the at least one imaging device, or of an expected eye location being based on previously registered images of the at least one eye.

Figure 2A:
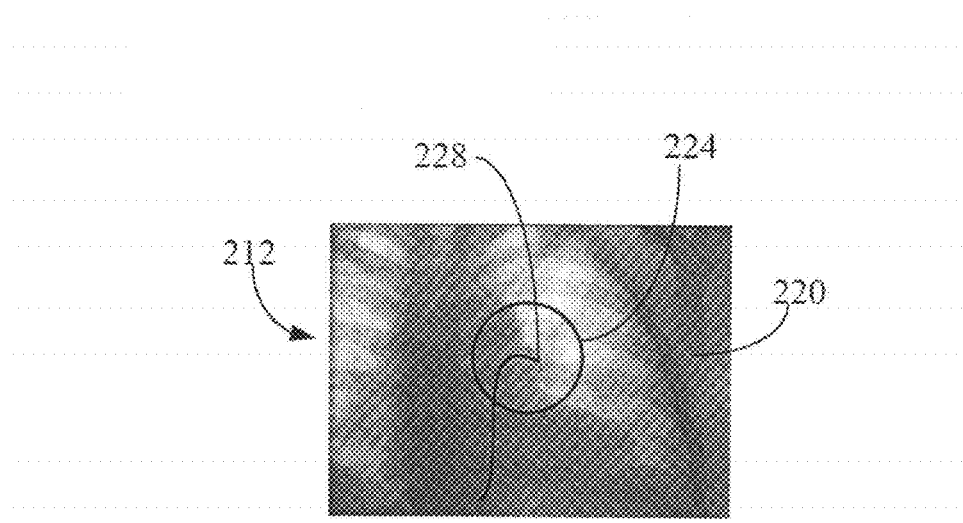
FIG. 2A is a fluoroscopic image of a treatment recipient segment obtained by the system of FIG. 2.
Figure 2:
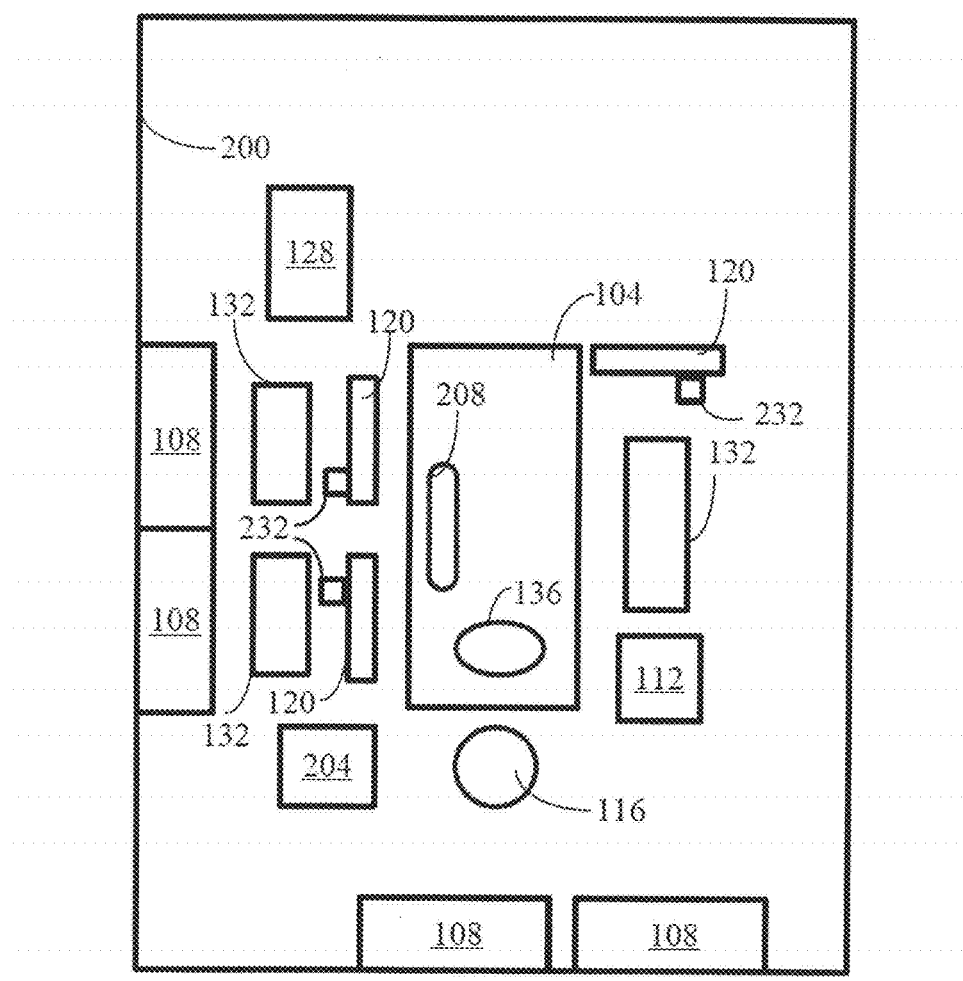
FIG. 2 is a block diagram of a system having a non-contact non-verbal interface for use in operating room according to an example.

With reference to FIG. 2, shown is an example of a block diagram of a system having a non-contact interface and non-verbal communication process for use in operating room. In particular system 200 includes a system controller 204. Controller 204 could by such as a PC or other computer connected to a monitor 208 and configured to display on the monitor 208 one or more fluoroscopic images 212 (FIG. 2A) of a treatment recipient segment 220 and in particular a ROI 224 including operating tool 228. Controller 204 could be configured to execute a number of procedures, for example, to operate various auxiliary devices, such as ECG device, treatment recipient table or support 104, field of view of the X-ray source 116, and other devices that could be present in the operating room, but are not shown. Procedures in the operating room are generally performed by an operating team including specialists of different medical professions. The operating room team could include imaging specialists, surgeons, cross trained physicians, cardiologists, anesthesiologists, nurses and others. Good communications and coordination between the operating team members could be a cornerstone of a successful catheterization process. Generally, an authorized team member or a team member highest in the hierarchy manages and prioritizes the tasks and procedures.

Among others, coordination and communication between the operating team members could be facilitated by including into system 200 one or more monitors 208 configured to display image 212 of a treatment area 220 including tissue 216 to be manipulated and a treatment tool 228. Each of the monitors 208 could include or communicate with a one or more of operating team members tracking devices 302.

Figure 3A:
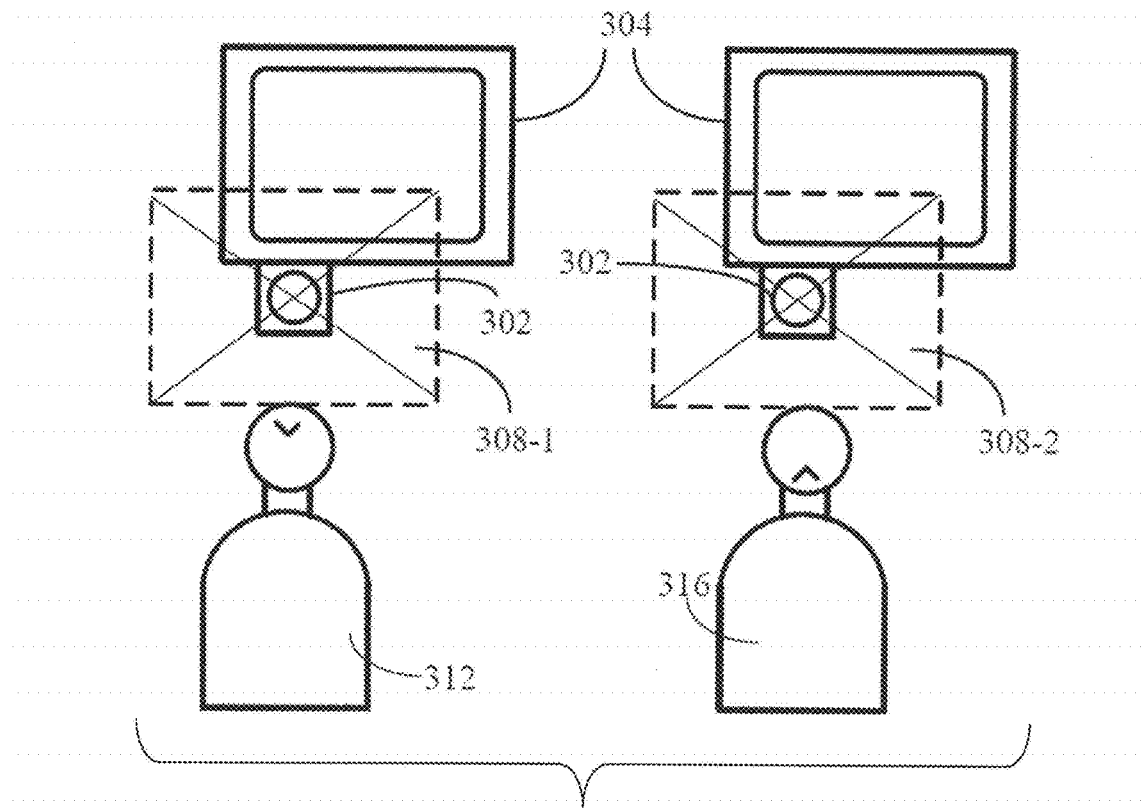
FIG. 3A is a schematic representation of a segment of a system for use in operation room having a non-contact interface for eye motion recognition according to an example.
Figure 3B:
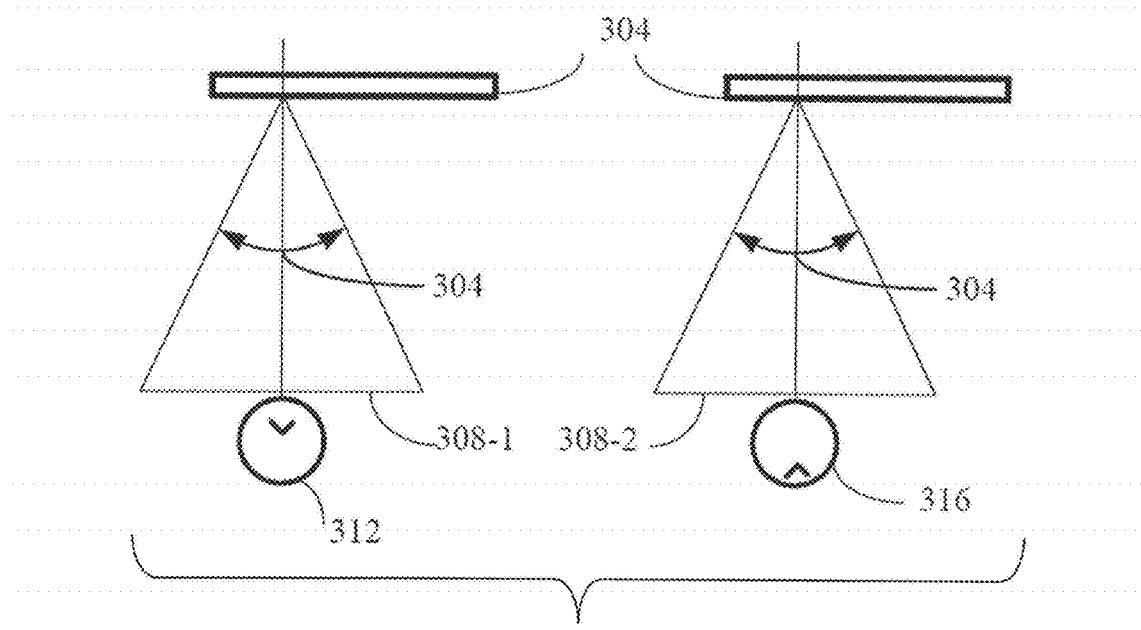
FIG. 3B is a schematic representation of a segment of a system for use in operation room having a non-contact interface for eye motion recognition according to another example.

FIG. 3A and FIG. 3B are schematic representations of a segment of a system for use in operation room having a non-contact interface for eye motion recognition according to an example. As illustrated, monitor 304 is located within main operating console of system 100 or 200, although there could be a number of operating consoles. An eye tracking device 302 such as for example, X2 Eye Trackers from Tobii Technology AB S-182 17 Danderyd Sweden or similar, could be mechanically coupled to monitor 208. Alternatively, a head mounted eye tracker that includes monitor tracking can also be used. Eye tracking device 302 usually includes an illuminator configured to illuminate the operating team member eye such that a reflection off the surface of the eye's cornea is generated. These reflections can be used to calculate the operating team member gaze point coordinates on monitor 304 along line of sight and communicate the coordinates to main 204 or auxiliary computer/controller 112 communicating with the main computer/controller 204 (FIG. 2). As disclosed above, the monitor displays on the screen a real time image of the treatment area 212 and the treatment tool 228 position. The monitor is configured to display the tool advancement, tool selection, tool configuration, and instructions to other team members.

Each of the operating team members tracking devices 302 has a field of view 304 and could be characterized by a particular viewing box 308. Generally, each eye tracking device 302 is configured to track one uniquely identified operating team member 312 or 316, although in some examples and in particular when one of the operating team members moves from one physical location to another physical location, two viewing boxes 308-1 and 308-2 could have partially overlapping area (volume) or their field of view. In one example, their field of view could be tangential with each other.

Each subject or operating team member taking place in the processes or workflow in the operating room could have one unique operating team member identifying characteristic. Such unique operating team member identifying characteristic could be certain anatomical characteristics of the operating team member (facial features), pressure developed by one of the limbs of the operating team member, and artificially generated or coded identifiers. Authentication of each of the operating team member could be performed before the member enters the operating room or prepared ahead of time and entered and stored in the system. For example, the anatomical characteristics of the operating team members could be prepared ahead of time in course of the system training course. In addition to anatomical characteristics of the operation team member additional unique identifying features could be entered into the system. These features could include the probability of positive operating team member identification. Additionally, storage of unique operating team members identifying features could support instant operating team members formation.

The anatomical characteristics of the operating team member could include facial outline, distance between eyes, skin hue, voice, fingerprint, and others. For example, a pressure sensor could be built-in or located in one or more of the foot or hand (limb) switches switching ON or OFF certain devices. Pressure applied to the switch by an authorized operating team member could be measured by the pressure sensor. The switch or pressure sensor could be configured to activate or facilitate activation of a particular device or function of the system. The artificially generated or coded identifier could be such as an RFID tag, a radiation counting (recoding and accumulating) tag attached to each operating team, and other suitable identifier. The radiation counting tag could accumulate and retain X-ray or other radiation dose that could be read off by a team member tracking device or communicated to the team member tracking device.

In some examples, the unique operating team member identifying characteristic could include the operating team member authorization permissions or the member status within the operation room team hierarchy. In some examples, the unique operating team member identifying characteristic, which is associated with each team member could be configured to communicate to the operating team member tracking device or the team member tracking device could identify the unique operating team member identifying characteristic. The operating team member tracking device could be configured to communicate or track one uniquely identified operating team member or a number of team members. The unique operating team member identifying characteristic facilitate tracking of a team member by the team member tracking devices that could be configured to distinguish between different operating team members and provide location coordinates of a uniquely identified team member to another tracking device.

Figure 4A:
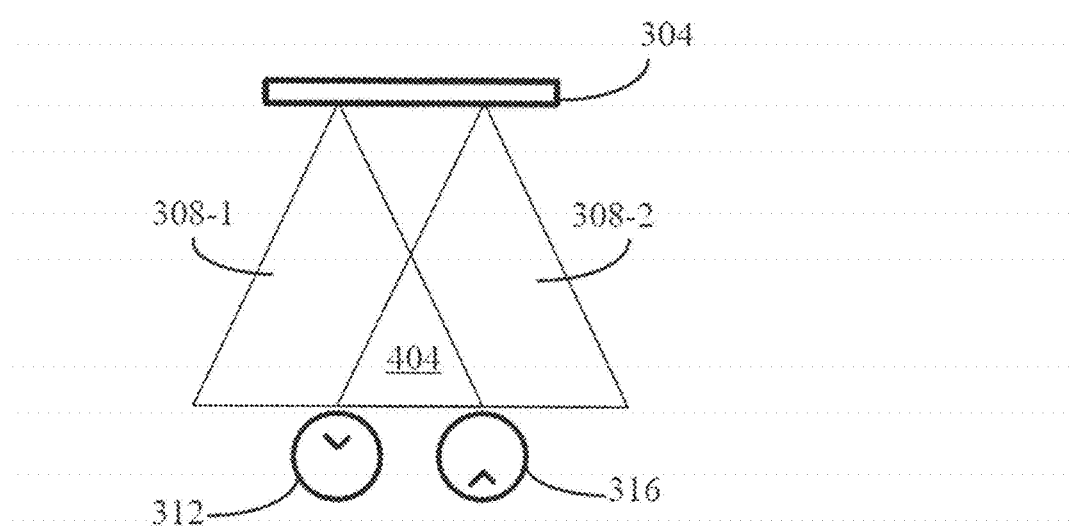
FIG. 4A is a schematic representation of viewing fields characterizing different situations according to an example.

The team member tracking devices could communicate between them and with the respective or central control unit and transfer between them team member identification features. For example, as shown in FIG. 4A when a physical location or activity of a first team member 312 changes relative to a physical location or activity of a second team member 316, a tracking device 302 with field of view 308-1 originally associated with the first team member 312 could be configured to pass on the unique team member identifying characteristic and team member monitoring to a second tracking device 302 with field of view 308-2. The transfer could take place when the fields of view of the first and second team member tracking devices overlap. The overlap value at which the first team member tracking device transfers the team member tracking to a second team member tracking device with overlapping viewing box could be set apriori. For example, when the overlap 404 is m/n or probability of the team member identification by the second team member tracking device is at least 75%. Other criteria for control transfer from one team member tracking device to another team member tracking device could be set also. For example, the transfer of the team member tracking could take place if probability of identifying a particular team member is higher than 20% or 25% or the probability of the team member identification is based on an arithmetical average of the last 20 or 30 team member identifications.

Figure 4B:
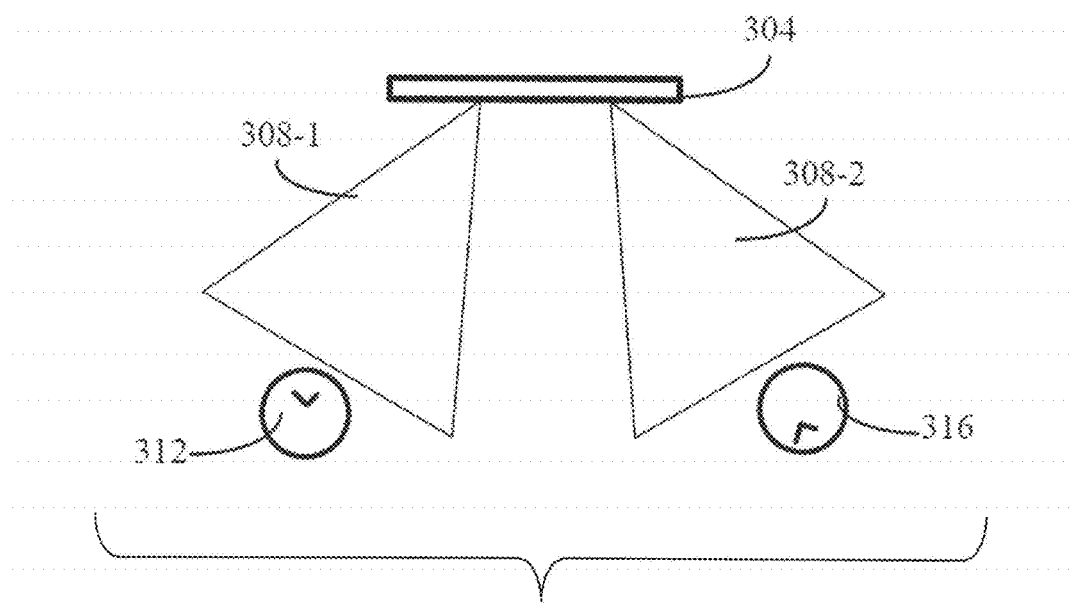
FIG. 4B is a schematic representation showing the tracking devices mounted at an angle relative to the monitor.

Another possibility could be to predetermine regions in which each team member tracking device operates. Using the example in FIG. 4A, two team member tracking devices 302 (for instance, Tobii X2 eye trackers) are mounted side by side beneath monitor 304. It would be appreciated that the number of operating team member tracking devices is not limited to two, and their placement is not limited to the simplified configuration illustrated in this example. For instance, the tracking devices could be mounted at an angle relative to the monitor as is depicted in FIG. 4B. Each tracking device is characterized by a viewing box which could be partially overlapping with one or more of the neighbor viewing boxes. When first operating team member 312 is located in viewing box 308-1 of the left of first operating team member tracking device, the left tracking device is activated to provide tracking and the right or second operating team member tracking device is deactivated to avoid emitted by the operating team member tracking devices infrared radiation interference.

When first team operating member 312 moves to overlap area 404, tracking can be performed by either operating team member tracking device. Using hysteresis, operating team member tracking in this area is maintained by the previously active tracker before the first operating team member entered the overlap area. When first team member 312 moves out of overlap area and into viewing box 308-2 of the right or second operating team member tracking device, operating team member tracking is thereupon transferred from the left or first tracking device to the right or second operating team member tracking device (in this example: left tracking device deactivates and right tracking device activates). The location of first operating team member 312 can be provided in this example by the Tobii X2 eye tracker, which calculates the operating team member's location relative to the viewing box. This location can signal to the system at which point to transfer operating team member tracking to another team member tracking device Alternatively, and according to the team member authorization, an authorized team member could initiate team member control transfer from one team member tracking device to another team member tracking device. The transfer of control could include transfer of certain team member authorization priorities.

In some examples at least one team member tracking device could be configured to operate as a master tracking device. A master tracking device could be configured to track simultaneously a plurality of the team members. This device could pass along the locations of the plurality of team members to other team member tracking devices. In the case where the team member tracking devices are eye trackers, a master tracking device could coordinate activation and deactivation of a plurality of team member tracking devices to avoid infrared radiation interference.

Figure 5:
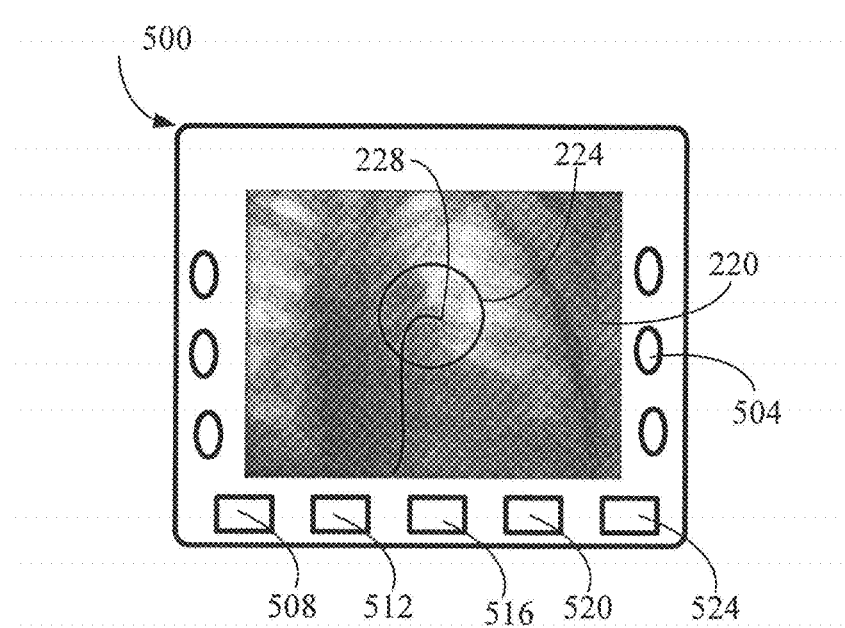
FIG. 5 is a schematic representation of monitor displaying an image configured for non-contact interface for eye motion recognition according to an example.

The image on the monitor screen (FIG. 5) could be configured to include an area where different button type or any other shape images 504, 508-524 could be displayed. Each of such button type images 504, 508-524, could be used to activate or perform certain function, activate a device, or transfer instructions to other operating team members.

The authorized operating team member, which could be the highest hierarchy team member or a team member acting on his behalf, gazes at a desired or target area on the monitor screen. The respective eye tracking device track continuously tracks the operating team member gaze point coordinates on monitor 500. The operating team member can concurrently select a tool or a function by gazing at a target area and setting it temporarily or at least for the current procedure as a default tool. The selected default tool would follow the authorized team member gaze, performing a desired surgical procedure, which could be catheter advance, or request for an additional tool and etc. Depending on authorization more than one operating team members could gaze at the same monitor. In one example, different operating team members could perform different tasks. In one example, some of the operating team members could concentrate or perform the same task. Such task, for example, could require participation of more than a single operating team member.

By gazing at a proper area on the screen of the monitor an authorized operating team member could select a desired or target treatment area and even change the magnification and position of the selected area on the screen. In one example, the magnification and position of the treatment area could be altered by changing the field of view or X-ray radiation spread angle and concentrating the X-rays in a smaller spatial angle. In another example, by gazing at a button activating the treatment recipient support and repositioning the support in space (translating the support horizontally, vertically and tilting the support) to hone in on coordinates provided by the tracking device.

The system could further include a device or a program configured to decode the selection made by the authorized operating team member and verify whether the selection action was decoded correctly and made by an authorized person.

Non-contact interface is an input/output device that allows the operating team members and system 200 to communicate with each other for monitoring and controlling a medical procedure without requiring the team member to touch any buttons, cursor or keyboard.

What is claimed is:

1. A method of monitoring and controlling a medical procedure comprising:
   displaying on at least one monitor at least one image of at least one treatment area including tissue to be manipulated and a treatment tool;
   tracking a plurality of team members using tracking devices having a field of view characterized by a viewing box with at least two team member tracking device viewing boxes having at least partially overlapping area (volume), each tracking device configured to track at least one uniquely identified team member;
   defining at least one identifier associated with each team member;
   communicating to each team member tracking device at least one unique team member identifying characteristic; and
   when a physical location (or activity) of a first team member changes relative to a physical location (or activity) of a second team member, passing on by a tracking device originally associated with the first team member the first team member identifier and the first team member monitoring to a second (partially overlapping) team member tracking device.

2. The method according to claim 1, wherein the team member identifier is one of a group of identifiers consisting of anatomical characteristics of the team member, pressure developed by at least one limb of the team member, and an artificially generated identifier.

3. The method according to claim 2, wherein the anatomical characteristics of the team member comprise at least one of facial outline, distance between eyes, skin hue, voice and fingerprint.

4. The method according to claim 2, wherein the pressure developed by at least one limb of the team member is pressure developed by one of a foot and a palm of the team member.

5. The method according to claim 4, comprising measuring the pressure developed by at least one limb of the team member.

6. The method according to claim 2, wherein the artificially generated identifier is one of an RFID tag and a radiation counting tag attached to the team member.

7. The method according to claim 1 wherein the team member identifier includes data on team member hierarchy, team member functionality, and team member authorizations.

8. The method according to claim 1, further comprising emergency overriding limitations associated with team member identifier preferences/authorizations/hierarchy.

9. The method according to claim 1, further comprising passing on the team member identifier and team member monitoring to a corresponding team member tracking device with partially overlapping field of view of viewing box when at least 75% of the view boxes field of view overlap.

10. The method according to claim 1, further comprising deactivating a first operating team member tracking device and activating a second team member tracking device in order to avoid infrared radiation interference, when the first operating team member tracking device passes on the first team member identifier and monitoring to the second team member tracking device.

11. The method according to claim 1, further comprising distinguishing by at least one of the tracking devices between different team members and providing location coordinates of a uniquely identified team member to another tracking device.

12. The method according to claim 11, said providing by the first tracking device, location coordinates of a uniquely identified team member to a corresponding designated tracking device is in accordance with a predetermined team member hierarchy.

13. The method according to claim 1, wherein said passing on the first team member identifier and team member monitoring to a corresponding second team member tracking device with partially overlapping viewing box is done when the probability of the team member identification by the second team member tracking device is at least 75%.

14. The method according to claim 13, wherein the probability of the team member identification is based on an arithmetical average of at least 20 last team members identifications.

15. The method according to claim 1, wherein at least one team member tracking device is a master tracking device, further comprising tracking simultaneously a plurality of the team members by said master tracking device.

16. The method according to claim 1, wherein at least one of said at least one monitor configured to display at least one image of at least one treatment area including tissue to be manipulated and a treatment tool, is responsive to team member gaze.

17. The method according to claim 16, further comprising activating at least one of a group of system processes consisting of treatment area and a treatment tool on screen position, tool advancement, tool selection, tool configuration, and instructions to other team members, by the monitor responsive to team member gaze.

18. The method according to claim 16, further comprising communicating by the monitor responsive to the team member gaze with the treatment recipient support and conveying to the support commands to translate horizontally, translate vertically and tilt to hone in on coordinates provided by the tracking device.

19. The method according to claim 16, further comprising selecting the tool by tracking point of gaze on screen.

20. The method according to claim 16, further comprising executing instructions to other team members by tracking point of gaze on screen.

\* \* \* \* \*